(12) United States Patent
Strang

(10) Patent No.: US 8,216,160 B2
(45) Date of Patent: Jul. 10, 2012

(54) FLEXIBILITY ASSESSMENT APPARATUS

(76) Inventor: Alan Wayne Strang, Oxley (AU)

( * ) Notice: Subject to any disclaimer, the term of this patent is extended or adjusted under 35 U.S.C. 154(b) by 697 days.

(21) Appl. No.: 12/306,762

(22) PCT Filed: Jun. 29, 2007

(86) PCT No.: PCT/AU2007/000897
§ 371 (c)(1),
(2), (4) Date: Dec. 29, 1980

(87) PCT Pub. No.: WO2008/003125
PCT Pub. Date: Jan. 10, 2008

(65) Prior Publication Data
US 2009/0312672 A1  Dec. 17, 2009

(30) Foreign Application Priority Data

Jul. 4, 2006 (AU) ................................ 2006903587
Apr. 3, 2007 (AU) ................................ 2007201433

(51) Int. Cl.
*A61B 5/103* (2006.01)
(52) U.S. Cl. ....................... 600/595; 482/907; 73/379.01
(58) Field of Classification Search .................. 482/907; 600/599, 595; 73/379.01
See application file for complete search history.

(56) References Cited

U.S. PATENT DOCUMENTS

| | | | | | |
|---|---|---|---|---|---|
| 5,567,202 | A | * | 10/1996 | Hager | 482/131 |
| 5,755,576 | A | * | 5/1998 | Dunn et al. | 434/258 |
| 5,935,087 | A | * | 8/1999 | Kobayashi | 600/595 |
| 6,422,981 | B1 | * | 7/2002 | Riser | 482/142 |
| 6,659,925 | B2 | * | 12/2003 | Wideman et al. | 482/148 |
| 7,207,932 | B1 | * | 4/2007 | Dean | 482/140 |
| 2005/0054499 | A1 | * | 3/2005 | Davies, III | 482/131 |
| 2005/0209055 | A1 | * | 9/2005 | Anders | 482/51 |
| 2006/0135332 | A1 | * | 6/2006 | Larson | 482/148 |

FOREIGN PATENT DOCUMENTS

| | | |
|---|---|---|
| JP | 200170286 | 3/2001 |
| RU | 2026007 | 1/1995 |
| SU | 1505503 | 9/1989 |

* cited by examiner

*Primary Examiner* — Max Hindenburg
*Assistant Examiner* — Michael C Stout
(74) *Attorney, Agent, or Firm* — Schmeiser, Olsen & Watts, LLP

(57) ABSTRACT

A sit and reach flexibility assessment apparatus comprises a spine with a measuring rule, footplates mounted on either side of the spine and rotatable out of the and at approximate right angles to the plane of the spine, and heel rests mounted at the base of the footplates and rotatable to a position at approximate right angles to the footplates and the spine. The apparatus also has storage compartments and a carry handle.

13 Claims, 3 Drawing Sheets

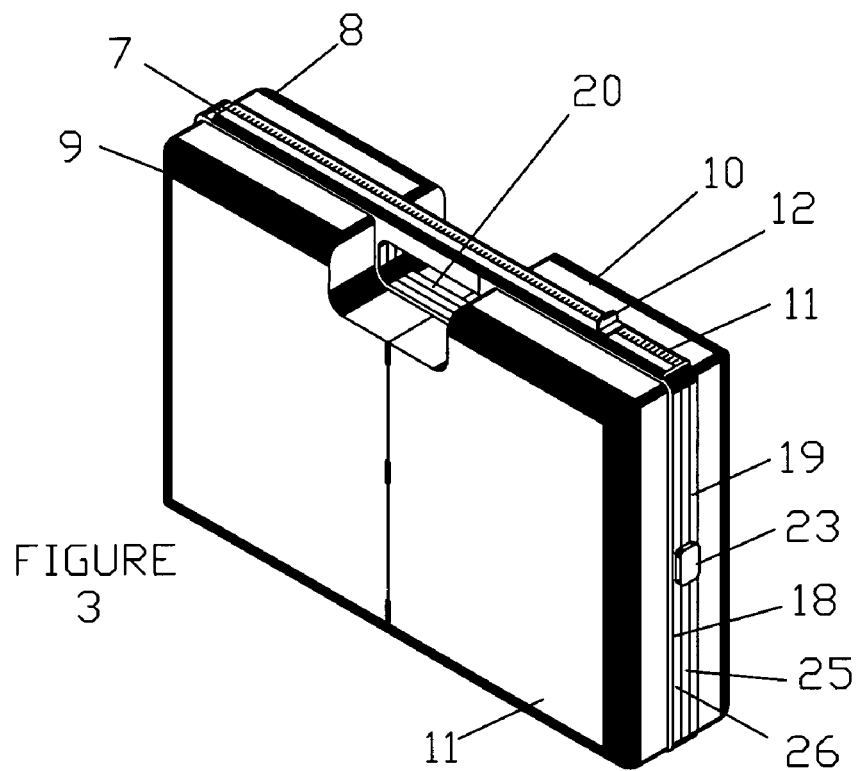
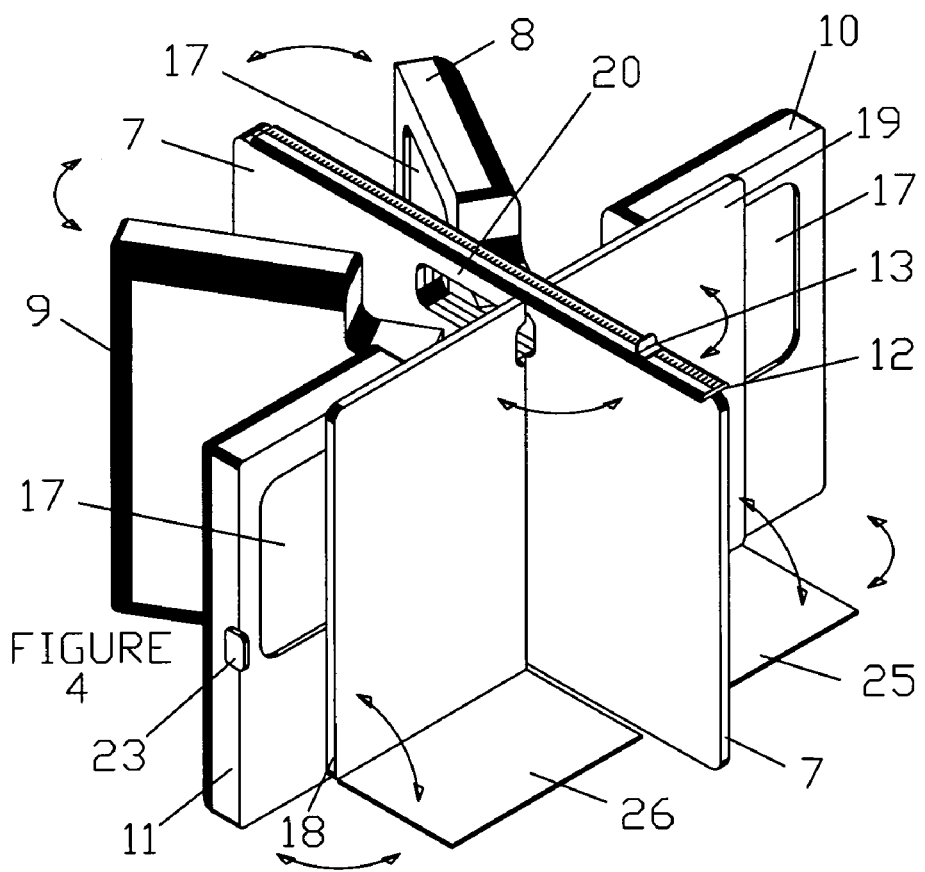

FLEXIBILITY ASSESSMENT APPARATUS

FIELD OF INVENTION

This invention relates to sit and reach flexibility assessment apparatus used in the fitness and health industry to measure hamstring and lower back flexibility.

BACKGROUND OF THE INVENTION

Apparatus to measure hamstring and lower back flexibility is well known in the health and fitness industry. For example the catalogues of the Australian company Hart Sport and the US company Lafayette Instrument show box like steel structures with a foot plate and a slide bar which moves on a linear scale to register an individual's maximum reach. However these structures are bulky and heavy to transport and store.

A primitive apparatus of this kind is illustrated in U.S. Pat. No. 6,821,257 which teaches a method for evaluating the likelihood of a person developing a back injury on a job which requires medium to heavy lifting and a variety of back movements. Although simple, this apparatus is bulky and has no scale for measuring reach which must be done by other means.

JP2001-70286 discloses an apparatus where the user sits in a frame with parallel rails extending at right angles to a wall with her back to the wall and pushes a tray like trolley along the rails to her maximum reach. This apparatus can be dismantled for transport but its reassembly is complex and time consuming. Also the calibration of the device to measure reach presents some difficulty.

OBJECT OF THE INVENTION

It is therefore an object of the present invention to provide a sit and reach flexibility assessment apparatus which overcomes the disadvantages of the prior art or at least provides a useful alternative to prior art devices.

STATEMENT OF THE INVENTION

According to the present invention a sit and reach flexibility assessment apparatus comprises a spine with a measuring rule, footplates mounted on either side of the spine and rotatable out of and at approximate right angles to the plane of the spine, and heel rests mounted at the base of the footplates and rotatable to a position at approximate right angles to the footplates and the spine.

Preferably the measuring rule has a slide indicator.

Preferably the spine has a carrying handle.

Preferably the spine has storage compartments mounted on either side away from the footplates.

Preferably the footplates have storage compartments mounted on their outer faces.

Preferably the footplate storage compartments slide out from the spine.

Preferably the storage compartments have lids which provide access.

In an alternative form of the apparatus the storage compartments away from the footplates also rotate out from the spine.

Preferably the storage compartments have access hatches in their inner faces.

Preferably the storage compartments are locked in the stowed position by latches.

A method of measuring hamstring and lower back flexibility with an apparatus which comprises a spine with a measuring rule, footplates mounted on either side of the spine and rotatable out of and at approximate right angles to the plane of the spine, and heel rests mounted at the base of the footplates and rotatable to a position at approximate right angles to the footplates and the spine.

In yet another form a sit and reach flexibility apparatus comprises a rectangular box structure, the inside base of which acts as a footplate and the lower side of which acts as a heel rest and a scale assembly which acts as a lid to the box and rotates through 270 degrees to sit on the top side of the box for measurement of a user's reach.

Preferably the scale assembly has a telescopic section which extends the reach of the scale.

Preferably the apparatus has storage compartments which pivot out from inside the box when the scale lid is rotated onto the top side of the box.

Preferably the top side of the box has a recessed handle which can be used to carry the apparatus when the scale lid is closed.

A method of measuring hamstring and lower back flexibility with an apparatus which comprises a rectangular box structure, the inside base of which acts as a footplate and the lower side of which acts as a heel rest and a scale assembly which acts as a lid to the box and rotates through 270 degrees to sit on the top side of the box for measurement of a user's reach.

BRIEF DESCRIPTION OF THE DRAWINGS

FIG. 3 is an isometric view of an alternative apparatus in a stowed configuration FIG. 4 is a view of the apparatus of FIG. 3 opened to its operating configuration

DETAILED DESCRIPTION OF THE INVENTION

Figure 1:
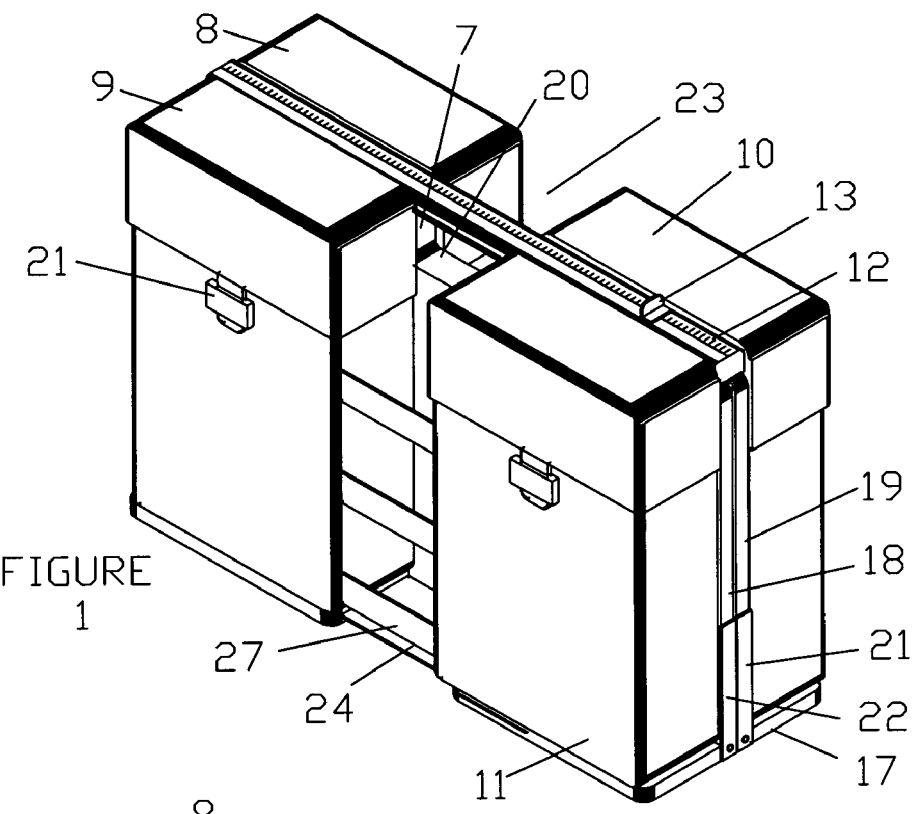
FIG. 1 is an isometric view of a flexibility apparatus in a stowed configuration
Figure 2:
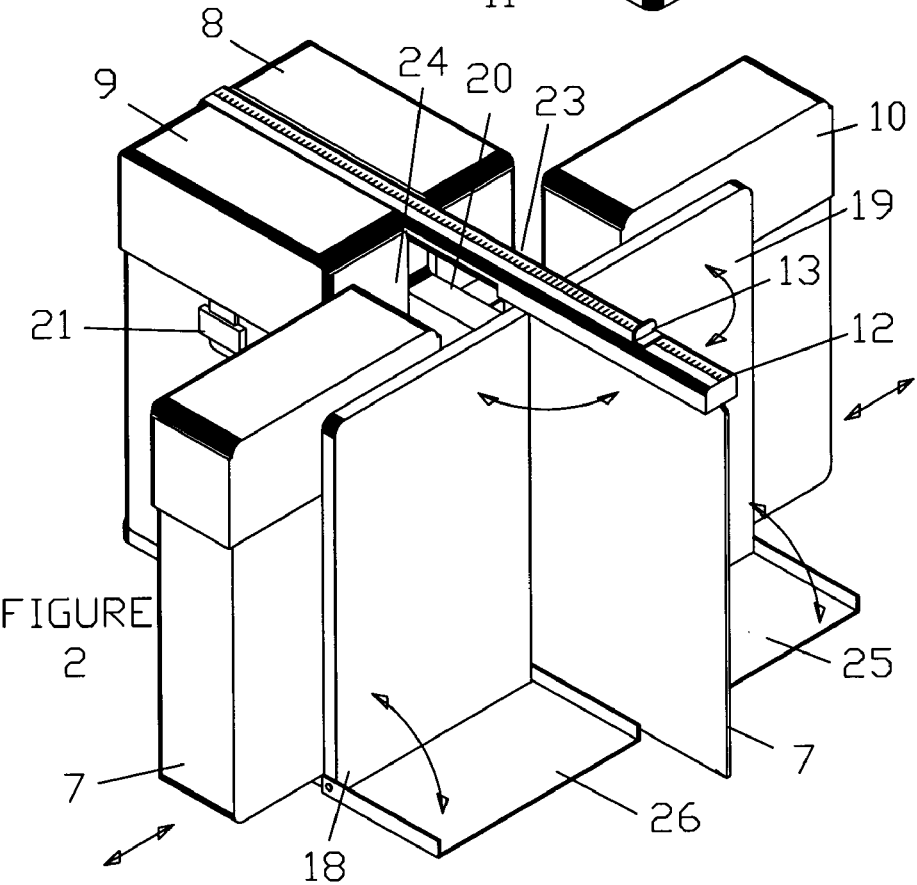
FIG. 2 is a view of the apparatus of FIG. 1 opened to its operating configuration

FIGS. 1 and 2 illustrate a flexibility apparatus with a central spine 7 on the top edge of which is mounted a measuring rule 12 with a slide indicator 13. Foot plates 18 and 19 are hinged vertically to plate 7 and fold out to stand at right angles to plate 7. Heel rests 25 and 26 fold down from foot plates 18 and 19 to rest the user's heels which thereby prevent the apparatus moving away during the reach phase.

Compartments 8 and 9 are fixed on the remote end of spine 7 and compartments 10 and 11 are slidably mounted on footplates 18 and 19. Boxes 8, 9, 10 and 11 have latches 21 and can be used for storage. Accordingly in the stored configuration of FIG. 1 the apparatus forms a carry case with handle 20, storage compartments 8, 9, 10 and 11 and compartments 23 and 24 formed between compartments 8 and 10 and 9 and 11 respectively which are connected by flexible straps 27.

In order to open the apparatus to the operating position of FIG. 2, foot plates 18 and 19 are rotated away from spine 7 and boxes 10 and 11 are slid out on foot plates 18 and 19. Heel rests 25 and 26 are then rotated down from foot plates 18 and 19. The user then places her feet on plates 18 and 19 and stretches forward to push indicator 13 as far along measuring rule 12 as she can. The resulting position of indicator 13 is the measure of the user's flexibility.

FIGS. 3 and 4 illustrate a more compact version of the apparatus with storage compartments 8, 9, 10 and 11 now provided with internal access hatches 17 instead of external lids. In this version compartments 8 and 9 as well as 10 and 11 rotate out from the spine to provide storage access and additional stability in use. In the stowed position of FIG. 3, clips 23 secure compartments 8, 9, 10 and 11 against spine 7 and the apparatus forms an attaché style case with handle 20.

Figure 5:
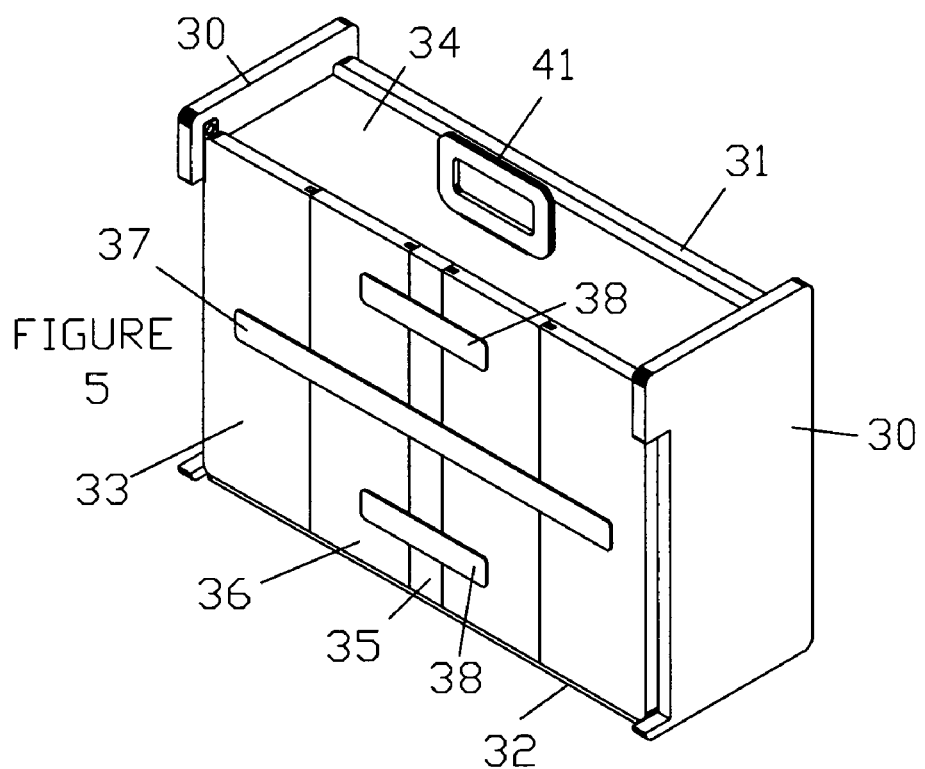
FIG. 5 is an isometric view of another alternative apparatus in a stowed configuration and FIG. 6 is a view of the apparatus of FIG. 5 opened to its operating configuration.
Figure 6:
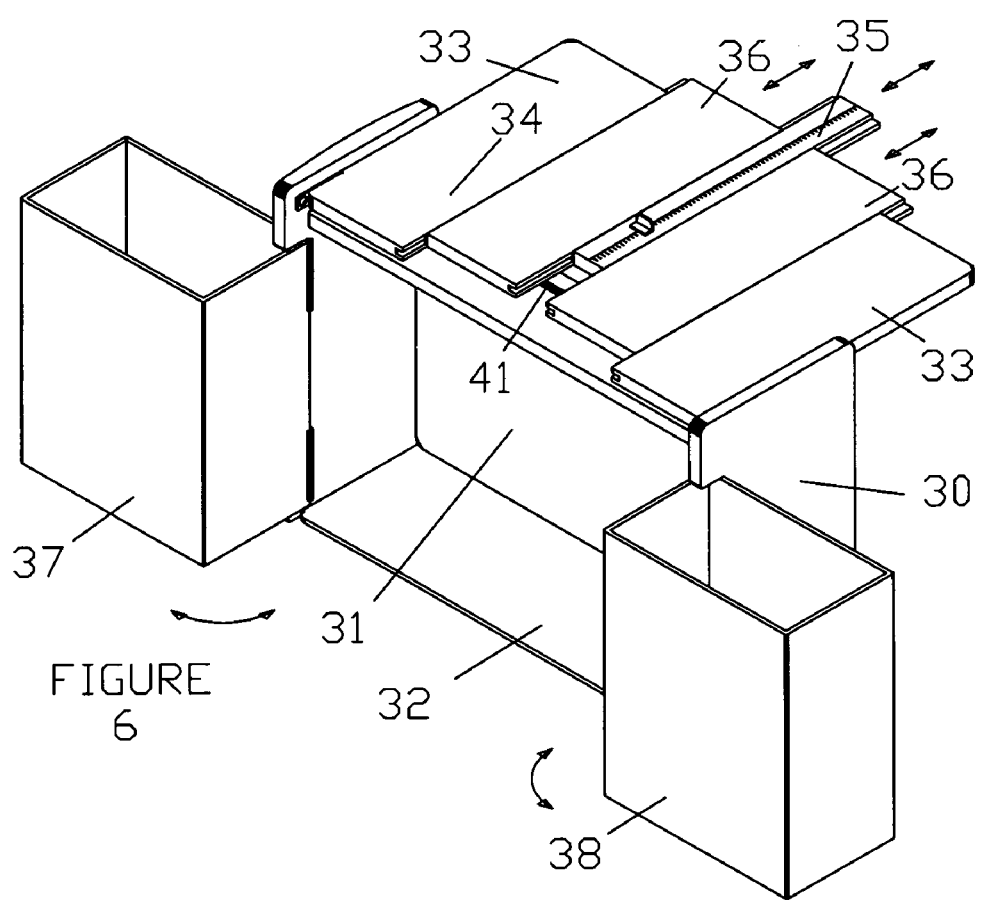

FIGS. 5 and 6 illustrate yet another version of the apparatus built on rectangular box 30, inside base 31 of which acts as a footplate and lower side 32 of which acts as a heel rest. Lid 33 is a scale assembly which pivots through 270 degrees to sit on top 34 of box 30. Lid 33 has a telescopic scale 35 and telescopic section 36 which extend scale 35 to accommodate a maximum reach. Lid sides 33 are connected by strap 37 and sections 36 by straps 38.

Storage compartments 37 and 38 pivot out of box 30 when lid 33 is in the operating configuration allowing base 31 and side 32 to act as a foot plate and a heel rest respectively. Handle 41 is recessed into top 34 and rotates upwards for carrying the apparatus in the stowed configuration.

VARIATIONS

It will be realized that the foregoing has been given by way of illustrative example only and that all other modifications and variations as would be apparent to persons skilled in the art are deemed to fall within the broad scope and ambit of the invention as herein set forth. For example central spine 7 can be provided with extensions of measuring rule 12 to increase the measuring range to accommodate the "modified" sit and reach test. Cut out handles 20 can be replaced with retrofitted handles which do not interfere with measuring rule 12. The apparatus can be fitted with wheels similar to those of modern luggage to facilitate portage. Central spine 7 can be replaced with a structure providing additional storage space accessed from the top or sides of the structure.

Further the apparatus may be electronically adapted with digital displays and specialized control features as well as audio and visual aids to more accurately measure the subject's flexibility. All such variations fall within the scope of the present invention. Throughout the description and claims to this specification the word "comprise" and variations of that word such as "comprises" and "comprising" are not intended to exclude other additives components integers or steps.

The invention claimed is:

1. A sit and reach flexibility assessment apparatus comprising:
    a spine with a measuring rule;
    a plurality of footplates mounted on either side of the spine and rotatable from a stowed position to an open position at right angles to a plane of the spine; and
    a plurality of heel rests mounted at a base of the plurality of footplates and rotatable to a position at right angles to the plurality of footplates and the spine.

2. The apparatus of claim 1 in which the measuring rule has a slide indicator.

3. The apparatus of claim 1 in which the spine has a carrying handle.

4. The apparatus of claim 1 in which the spine has a plurality of storage compartments mounted on either side away from the plurality of footplates.

5. The apparatus of claim 1 in which the plurality of footplates have a plurality of storage compartments mounted on an outer face of the plurality of footplates.

6. The apparatus of claim 5 in which the plurality of footplate storage compartments slide out from the spine.

7. The apparatus of claim 4 in which the plurality of storage compartments have lids which provide access.

8. The apparatus of claim 4 in which the plurality of storage compartments rotate out from the spine.

9. The apparatus of claim 4 in which each of the plurality of storage compartments have an access hatch in an inner face.

10. The apparatus of claim 4 in which the plurality of storage compartments are locked in a stowed position by a plurality of latches.

11. A method of measuring hamstring and lower back flexibility with an apparatus comprising:
    a spine with a measuring rule;
    a plurality of footplates mounted on either side of the spine and rotatable out of and at right angles to a plane of the spine; and
    a plurality of heel rests mounted at a base of the plurality of footplates and rotatable to a position at right angles to the plurality of footplates and the spine.

12. The apparatus of claim 1, wherein the plurality of heel rests are configured to fold down from the plurality of footplates to rest a user's feet, thereby preventing the apparatus from moving away in a reach phase of the user.

13. The method of claim 11, wherein the plurality of heel rests are configured to fold down from the plurality of footplates to rest a user's feet, thereby preventing the apparatus from moving away in a reach phase of the user.

* * * * *